(12) United States Patent
Dutta et al.

(10) Patent No.: US 7,774,040 B1
(45) Date of Patent: Aug. 10, 2010

(54) METHOD AND APPARATUS OF MULTI-PHASE CARDIAC IMAGING

(75) Inventors: Sandeep Dutta, Waukesha, WI (US); Aleksandar Zavaljevski, Waukesha, WI (US); Roy Nilsen, Menomonee Falls, WI (US); Darin R. Okerland, Muskego, WI (US); Rajendra Kurady, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 2017 days.

(21) Appl. No.: 10/250,268

(22) Filed: Jun. 19, 2003

(51) Int. Cl.
*A61B 5/05* (2006.01)

(52) U.S. Cl. .................. 600/407; 600/410; 600/425; 600/428; 600/436; 600/437; 378/8; 378/15

(58) Field of Classification Search ........... 600/407, 600/410, 425, 428, 436, 437; 364/413; 128/653; 378/8, 15
See application file for complete search history.

(56) References Cited

U.S. PATENT DOCUMENTS

| | | | |
|---|---|---|---|
| 6,154,516 A * | 11/2000 | Heuscher et al. | 378/15 |
| 6,233,478 B1 * | 5/2001 | Liu | 600/428 |
| 6,334,847 B1 * | 1/2002 | Fenster et al. | 600/443 |
| 6,408,043 B1 * | 6/2002 | Hu et al. | 378/8 |
| 6,504,894 B2 | 1/2003 | Pan et al. | |
| 7,289,841 B2 * | 10/2007 | Johnson et al. | 600/431 |
| 2004/0006268 A1 * | 1/2004 | Gilboa et al. | 600/424 |
| 2004/0019275 A1 * | 1/2004 | Iatrou et al. | 600/428 |

\* cited by examiner

*Primary Examiner*—Brian Casler
*Assistant Examiner*—Joel M Lamprecht
(74) *Attorney, Agent, or Firm*—Ziolkowski Patent Solutions Group, SC

(57) ABSTRACT

A method and apparatus for multi-phase cardiac CT imaging includes an adaptive, selective reconstruction process that, when possible, implements an image or non-phase location driven reconstruction process to reconstruct cardiac CT images. If the hardware parameters support an image location driven reconstruction for the particular imaging session then the image location driven reconstruction is implemented. However, if image location driven reconstruction is not supported, a default phase location driven reconstruction is employed. Image location driven reconstruction improves system throughput and improves image quality as more cardiac phase locations can routinely be generated to better "freeze" the motion of the heart of a patient.

21 Claims, 4 Drawing Sheets

METHOD AND APPARATUS OF MULTI-PHASE CARDIAC IMAGING

BACKGROUND OF INVENTION

The present invention relates generally to computed tomography imaging and, more particularly, to a method and apparatus of multi-phase cardiac CT imaging.

The narrowing or constriction of vessels carrying blood to the heart is a well-known cause of heart attacks and, gone untreated, can lead to sudden death. In such stenotic vessels, it is known that the region immediately downstream from the constriction is characterized by having rapid flow velocities and/or complex flow patterns. In general, narrowing of blood carrying vessels supplying an organ will ultimately lead to compromised function of the organ in question, at best, and organ failure, at worst. Quantitative flow data can readily aid in the diagnosis and management of patients and also help in the basic understanding of disease processes. There are many techniques available for the measurement of blood flow, including imaging based methods using radiographic imaging of contrast agents, both in projection and computed tomography (CT), ultrasound, and nuclear medicine techniques. Radiographic and nuclear medicine techniques often require the use of ionizing radiation and/or contrast agents. Some methods involve making assumptions about the flow characteristics which may not necessarily be true in vivo or require knowledge about the cross-sectional area of the vessel or the flow direction.

CT is one technique of acquiring blood flow and other cardiac data. Typically, in CT imaging systems, an x-ray source emits a fan-shaped beam toward a subject or object, such as a patient or a piece of luggage, for example. Hereinafter, reference to a "subject" shall include anything capable of being imaged. The beam, after being attenuated by the subject, impinges upon an array of radiation detectors. The intensity of the attenuated beam of radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to a data processing system for subsequent image reconstruction by an image reconstructor.

Cardiac reconstruction represents a significant portion of the processing required for CT cardiac imaging applications. The number of images to be reconstructed in cardiac studies can be quite large, especially if multiple phases of cardiac images are prescribed. Multiple phases are required for some cardiac applications such as left ventricular (LV) function where ejection fraction is calculated and LV wall motion is assessed. As such, it is not uncommon for 10 to 20 distinct phase locations to be required adequate temporal sampling. Likewise, multiple phases are desirable for imaging the coronary arteries as several phases may be required, frequently 3 or 6 phases, to sufficiently "freeze" the motion of the major arteries.

In multi-phase reconstruction it is generally known that the same scan data could be used for making images at the same location over a number of phases of the cardiac cycle. Known multi-phase reconstruction techniques reconstruct images for one phase at a time in what is generally referred to as a phase location driven reconstruction process. With this reconstruction technique, images for one phase are reconstructed for all imaging locations before proceeding with image reconstruction for another phase. As a result, to reconstruct all the multi-phase images, it is necessary to retrieve from memory and preprocess the same scan data a multiple number of times. These iterations decrease the performance and lengthen the time of the overall imaging process.

Therefore, it would be desirable to design an apparatus and method of multi-phase cardiac CT imaging that adaptively selects between a phase location driven reconstruction process and a more time efficient non-phase location driven reconstruction process.

BRIEF DESCRIPTION OF INVENTION

The present invention is a directed method and apparatus for multi-phase cardiac CT imaging overcoming the above drawbacks. The invention includes an adaptive, selective reconstruction process that, when possible, implements an image or non-phase location driven reconstruction process to reconstruct cardiac CT images. If the hardware parameters support an image location driven reconstruction for the particular imaging session then the image location driven reconstruction is implemented. However, if image location driven reconstruction is not supported, a default phase location driven reconstruction is employed. Image location driven reconstruction improves system throughput and improves image quality as more cardiac phase locations can routinely be generated to better "freeze" the motion of the heart of a patient.

Therefore, one aspect, the present invention includes a method of multi-phase cardiac images comprising the steps of acquiring views of image data for a number of prescribed phases for a number of imaging locations of a field-of-view (FOV) over a series of cardiac cycles of a subject and assessing operational parameters of an image reconstruction system. The method also includes the step of selecting, based on the operational parameters, one of a phase location driven reconstruction process that reconstructs images from views for all the number of imaging locations for one phase before reconstructing images for another phase and an image location driven reconstruction process that reconstructs images from views for all the prescribed phases for one imaging location before reconstructing images for another imaging location.

According to another aspect, the present invention includes a CT cardiac imaging system comprises an EKG machine to obtain an EKG recording of a patient indicative of a cardiac cycle of the patient. The system further includes a CT imaging apparatus comprising a data acquisition module including a rotatable gantry having a bore therethrough designed to receive the patient being translated through the bore by a movable table, the rotatable gantry having an x-ray source and an x-ray detector disposed therein to emit a fan beam of x-rays toward the patient and receive x-rays attenuated by the patient, respectively. The CT imaging apparatus further includes a computer programmed to control the data acquisition module to acquire CT data of the patient as a function of the cardiac cycle of the patient and determine if the CT imaging apparatus supports an image driven location reconstruction process wherein images are generated for all phases of the cardiac cycle at a first location before generating images at a second location and, if not, initialize a default phase location driven reconstruction process wherein images are generated at all locations for a first phase of the cardiac cycle before generating images for a second phase of the cardiac cycle.

In another aspect, the invention includes a computer readable storage medium having a computer program to adaptively select between CT reconstruction techniques, the computer program representing a set of instructions that when executed by a computer causes the computer to execute one acquisition data restore from a disk and calibration processing for a set of views needed to reconstruct a series of images for a plurality of z-locations for all measured phases of a cardiac cycle. The set of instructions then causes the computer to determine at least a portion of the set of views that are needed for reconstructing images at a first z-location for all measured phases of the cardiac cycle and reconstruct an image at the first z-location for all measured phases of the cardiac cycle before reconstructing an image at a next z-location.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The operating environment of the present invention is described with respect to a multi-slice computed tomography (CT) system configured to acquire CT data for multiple phases of a cardiac cycle. Moreover, the present invention will be described with respect to the detection and conversion of x-rays. However, one of ordinary skill in the art will further appreciate, that the present invention is equally applicable with the detection and conversion of other high frequency electromagnetic energy. Additionally, the present invention will be described with respect to a "third generation" CT imaging system, but is equally applicable with other CT imaging systems.

Figure 1:
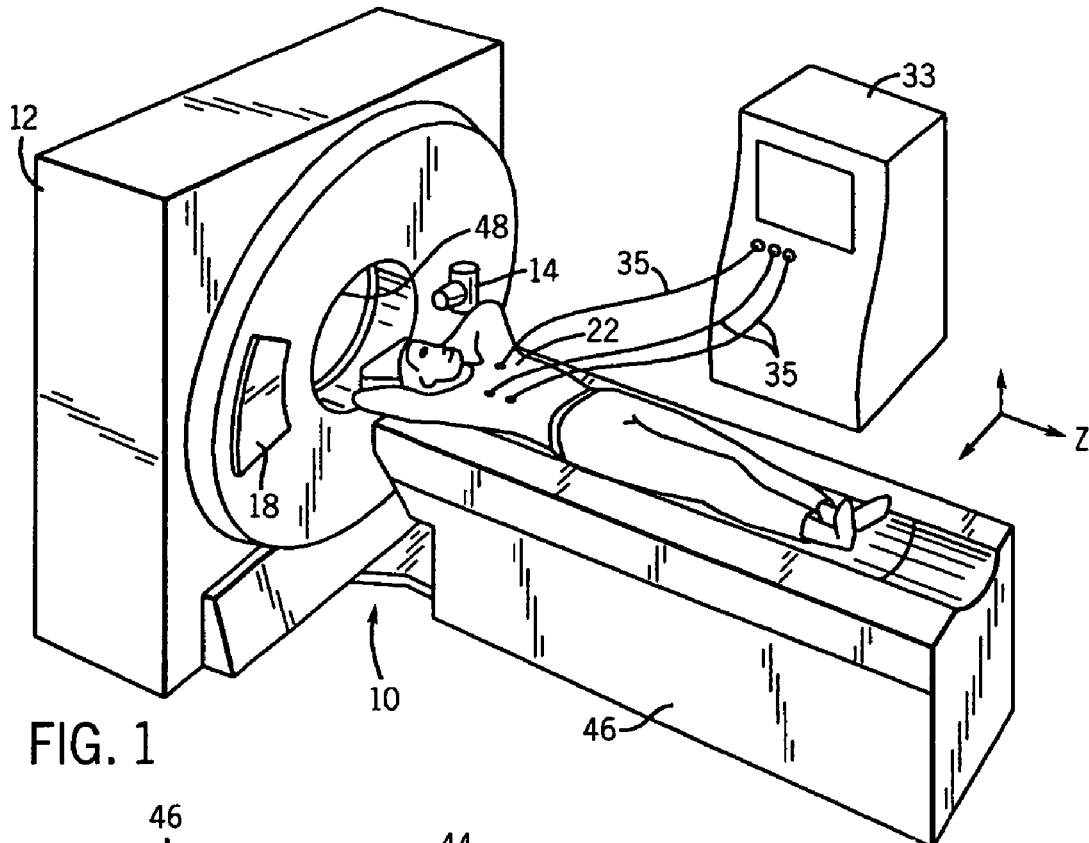
FIG. 1 is a pictorial view of a CT-EKG imaging system.
Figure 2:
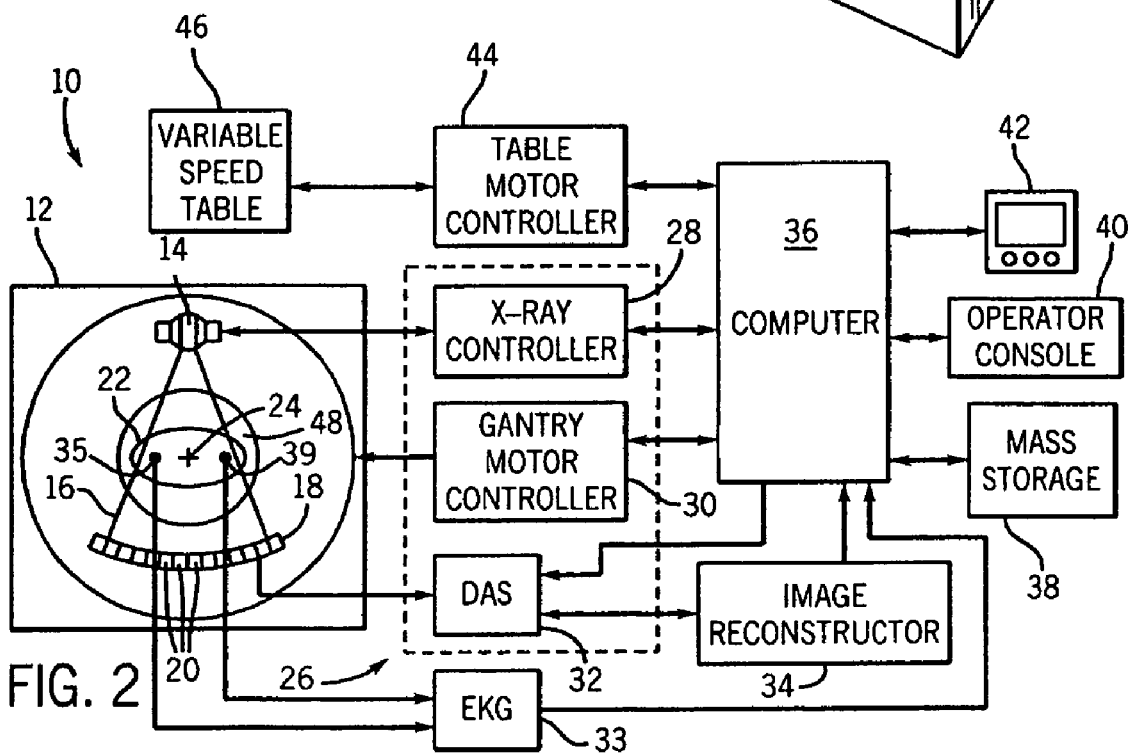
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. As will be described below, computer 36 also receives EKG signals from an EKG 33 connected to the subject via leads 35 to acquire cardiac data of the subject 22. The computer 36 correlates the EKG signals to determine the phases of the cardiac region. Preferably, the EKG machine 33 obtains an EKG recording of the patient before scanning commences such that data acquisition can be timed to occur during quiescent periods between peaks of a cardiac cycle. During these quiescent periods, the heart is relatively still and, therefore, it is preferred for data acquisition to occur during these portions of the cardiac cycle to minimize motion artifacts in the final reconstructed image. An image reconstructor 34 receives sampled and digitized x-ray data from DAS 32 and based on the correlation performs high speed reconstruction. The reconstructed image is stored in a mass storage device 38.

Computer 36 also receives commands and scanning parameters from an operator via console 40 that includes a keyboard, a data entry module, or the like. An associated display 42 allows the operator to observe the input data and the reconstructed images or other data from computer 36. The operator supplied commands and parameters are used by computer 36 to provide control signals and information to DAS 32, x-ray controller 28, EKG 34, and gantry motor controller 30. In addition, computer 36 operates a table motor controller 44 which controls a motorized table 46 to position patient 22 and gantry 12. Particularly, table 46 systematically moves patient 22 through a gantry opening 48 for data acquisition.

The present invention is directed to an adaptive and selective multiphase cardiac CT reconstruction process that selects and implements a particular reconstruction process based on the particular imaging session and operational parameters of the CT system. The process reduces both image reconstruction time as well as the time necessary for multiphase studies. The process is applicable with any type of multiphase cardiac study and may be implemented with other gated imaging techniques such as respiratory gated reconstruction.

Figure 3:
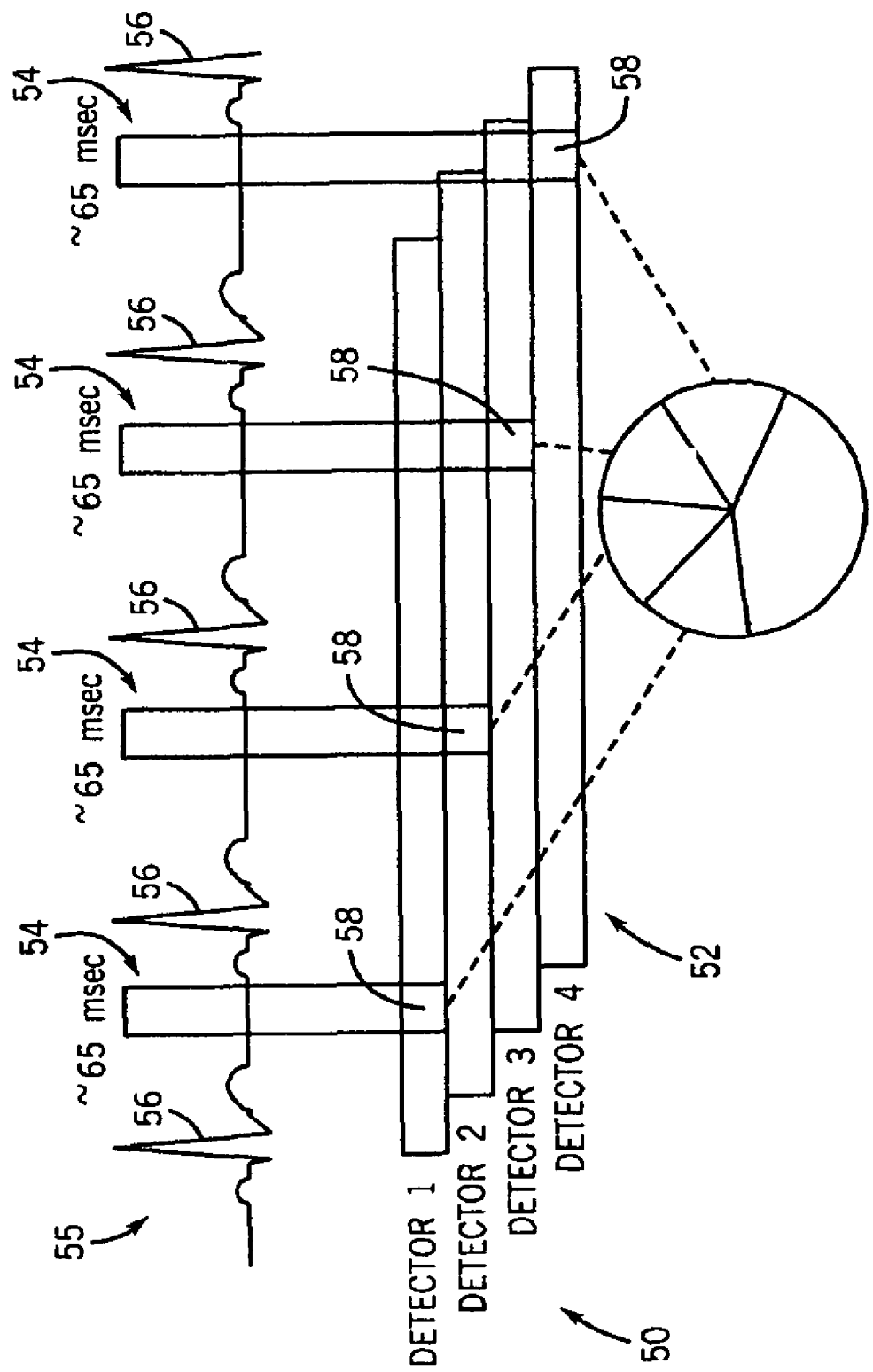
FIG. 3 is a schematic representation of multi-phase cardiac CT reconstruction.

Referring now to FIG. 3, a multi-sector reconstruction where portions of data are taken from multiple cardiac cycles at the same phase location to reconstruct an image is schematically shown and illustrates that a segmented image may be created from an EKG gated view data stream for a particular phase location. With this reconstruction technique, up to four sectors of data are used from four consecutive cardiac cycles to produce a complete image. Specifically, four detectors 50 acquire raw unprocessed data 52 from a cardiac region of a patient for four consecutive cardiac cycles 54 of a cardiac signal. Each of the cardiac cycles is defined by an R-R peak 56 in the cardiac signal and from the R-peak data it is possible to obtain phase information. Accordingly, the reconstruction process uses data for the same phase 58 for more than one cardiac cycle 54 of the cardiac signal 55 to reconstruct an image.

Figure 4:
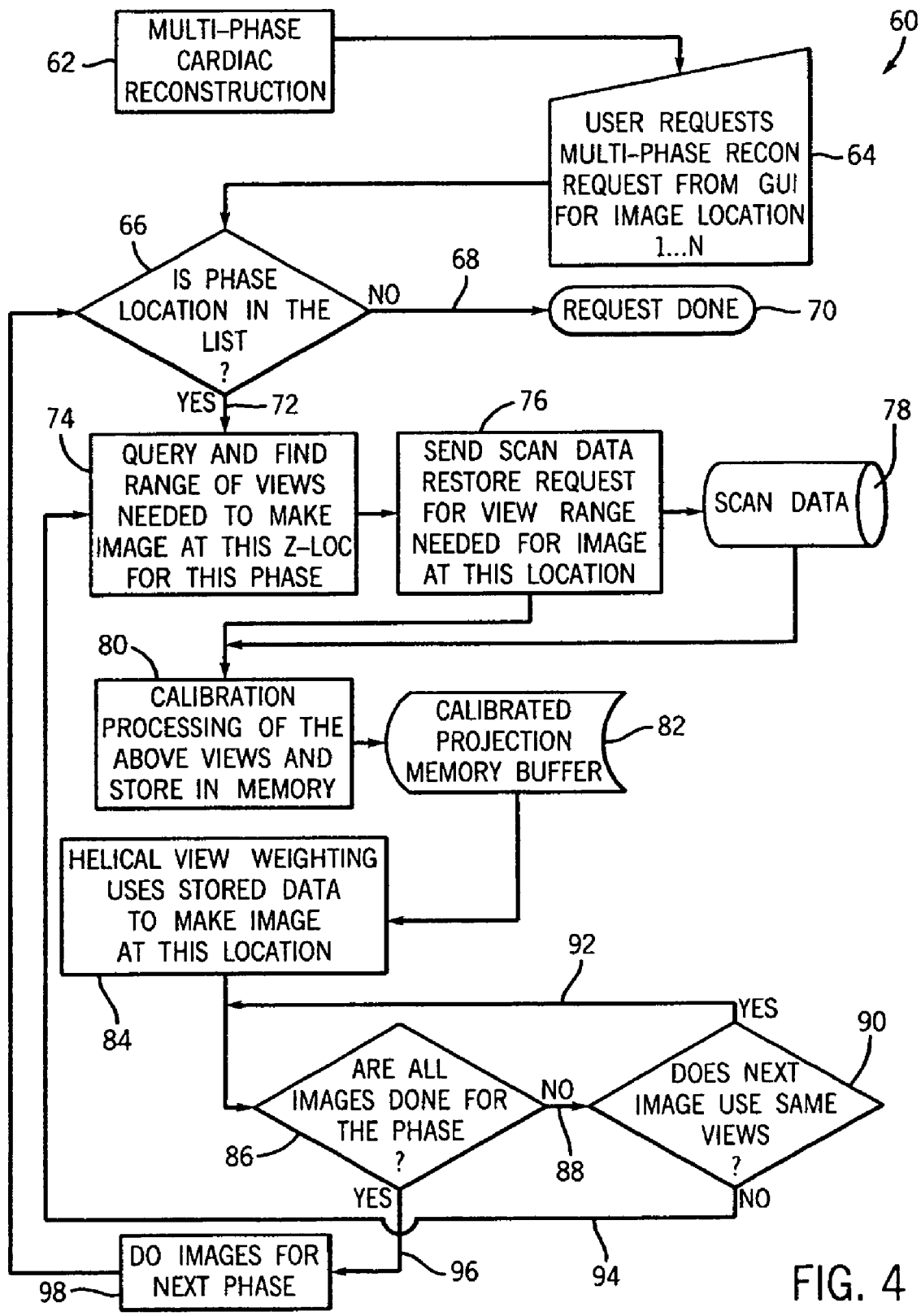
FIG. 4 is a flow chart setting forth the steps of an image location driven multiphase cardiac CT reconstruction.

Referring now to FIG. 4, the steps of a conventional phase location driven reconstruction process are set forth. In accordance with the present invention, the conventional phase location driven reconstruction process is a default reconstruction process if the CT system cannot support an image location driven reconstruction process for the particular imaging session or study. The conventional reconstruction process 60 begins at 62 with the initiation of a multiphase cardiac reconstruction. In this regard, the raw CT data has been acquired from the subject and stored in memory on a disk of the CT system or other archival location. The user or other operator then selects on a GUI or other selection interface a particular phase to be reconstructed 64. At 66, a determination is made as to whether the phase identified at 64 is included in the list of phase locations for which data was acquired. If not 66, 68, the reconstruction process is aborted and the user is notified accordingly at 70. If the selected phase is in the list 66, 72, the process continues at 74 with the querying and finding of the range of views needed to make images at the user-identified phase.

As described above, process 60 relates to the reconstruction of images based on data acquired during a CT data acquisition. Use of the term "views" relates to the data acquired during the CT data acquisition and represents the raw and unprocessed data acquired and stored in memory of the CT system. Accordingly, once the appropriate views have been queried and found 74, a request for a scan data restore for view range needed at the user-identified phase is made 76. The data stored in memory is then scanned at 78 in compliance with the request made at 76. The data is scanned to call-up or restore from memory the range of views necessary to reconstruct images for the user-identified phase. Once the data has been scanned, the data or views undergo calibration and processing at 80. The calibrated and processed data is then stored in a projection memory buffer at 82. The data in the projection memory buffer then undergoes helical view weighting at 84. Helical view weighting includes application of an algorithm that applies interpolation weights to the data. The algorithm may use data from multiple rotations or data from a single rotation to determine the appropriate weighting factors depending on the type of reconstruction to be carried out. Further, the helical view weighting may be replaced with a process that selects the appropriate views or data for back projection processing. Regardless of the weighting algorithm applied, the weighting is applied only to those views necessary to reconstruct an image(s) for the user-identified phase.

After the helical view weighing and associated image reconstruction, a determination is made as to whether all the images for all z-locations for the selected phase have been reconstructed 86. If not 86, 88, process 60 determines if the next image or z-location to be reconstructed uses the same set of views used to reconstruct images at the previous image location 90. If yes 90, 92, helical view weighting is once again applied and images for the next image location for the user selected phase are reconstructed. If not 90, 94, the process returns to step 74 with a querying and location of the range of views needed to generate an image at the next image location. It should be noted that at this stage, process 60 is still carrying out a reconstruction for the same phase identified by the user at 64. That is, reconstruction of the next phase or another phase does not commence until images for all image or z-locations at the first phase have been reconstructed. Accordingly, if all the prescribed images have been reconstructed for all z-locations at the first user-identified phase 86, 96, process 60 continues to step 98 with a prompt to the user to authorize reconstruction of images for the next phase. If the user authorizes reconstruction for the next phase at 98, the process returns to step 66 for subsequent processing as heretofore described.

Figure 5:
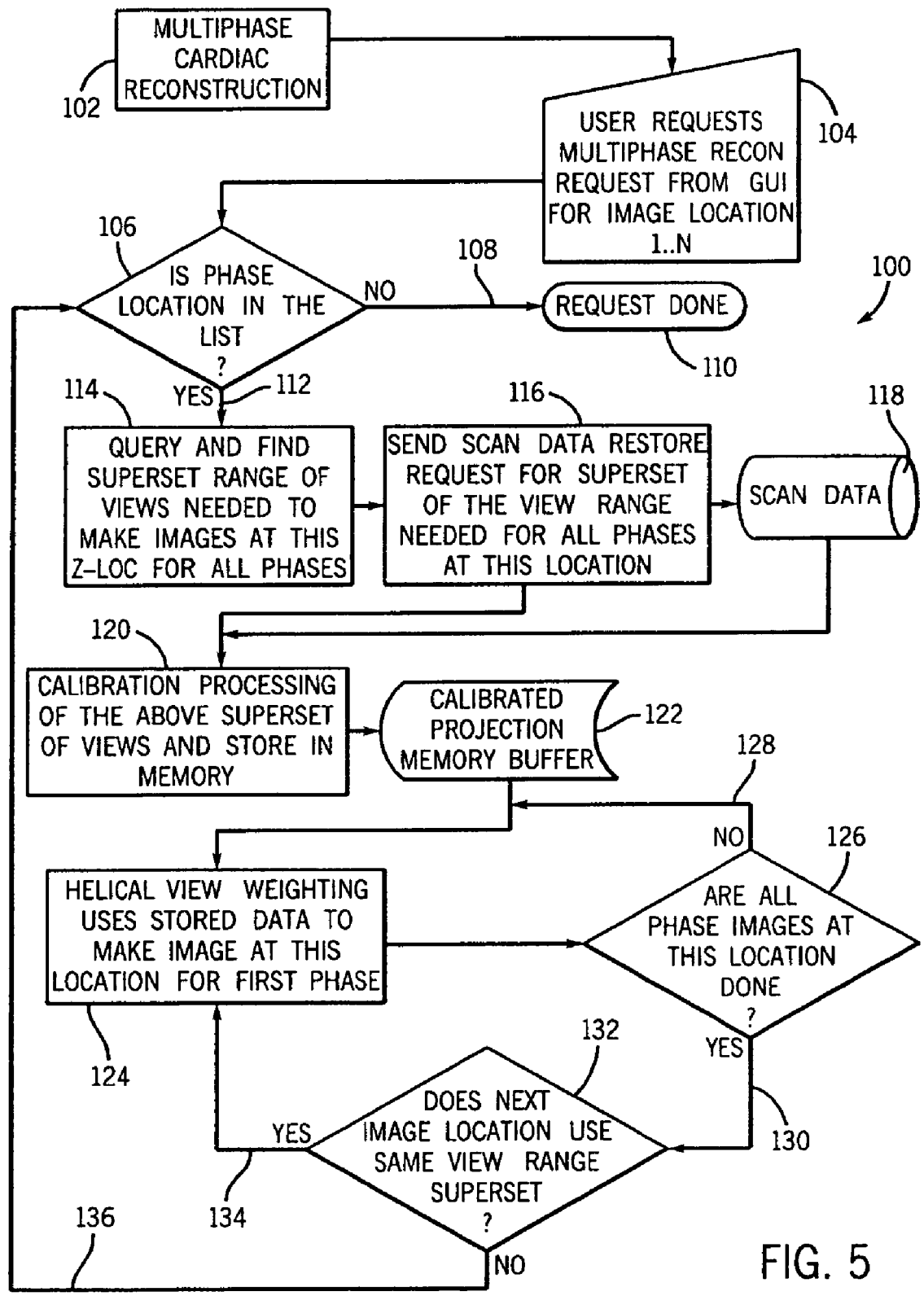
FIG. 5 is a flow chart setting forth the steps of a phase location driven multiphase cardiac CT reconstruction.

Process 60 described with respect to FIG. 4 is a default phase location driven multiphase cardiac reconstruction that is carried out if the CT system does not have sufficient temporary memory or buffer space to support an image location driven multiphase cardiac reconstruction such as that illustrated in FIG. 5. As will become evident, the image location driven process affords substantial reconstruction time savings through minimization of the restoration of raw data from memory typically associated with phase location driven reconstruction.

Referring now to FIG. 5, process 100 begins at 102 with the initiation of a multiphase cardiac reconstruction. The user or other operator then selects on a GUI or other selection interface a particular image location to be reconstructed 104. The identified image location corresponds to a particular location along a z-axis that extends parallel to the patient and patient table. At 106, a determination is made as to whether the image location identified is included in the list of image locations for which data was acquired. If not 106, 108, the reconstruction process is aborted and the user is notified accordingly at 110. If the image location identified is in the list 106, 112, the process continues at 114 with the querying and finding a superset range of views needed to make images at the user-identified image location for all phases.

Once the appropriate superset of views have been queried and found 114, a request for a scan data restore for view range needed at the user-identified location for all phases is made 116. The data stored in memory is then scanned at 118 in compliance with the request made at 116. The data is scanned to call-up or restore from memory the range of views necessary to reconstruct images for the user-identified location. Once the data has been scanned, the data or views undergo calibration and processing at 120. The calibrated and processed data is then stored in a projection memory buffer at 122. Process 100 is only possible if the CT system has a memory buffer of sufficient size to support temporary storage of the calibrated data for all phases at the user identified location. The size of the buffer needed varies and depends upon the number of views identified at 114. The data in the projection memory buffer then undergoes helical view weighting at 124 to make an image for the image location at the first phase.

After the calibrated superset range of views undergoes view weighting for making an, image at the z-location for the first phase a determination is made at 126 whether all the phases for the z-location have been imaged. If not 126, 128, process 100 returns to step 124 with the application of helical view weights to the calibrated superset range of views to make an image for the next phase at the z-location. As such, steps 124-128 repeat until all phases for the z-location identified at step 104 are imaged before proceeding to image reconstruction for another or next z-location. Accordingly, if the phases for the z-location have been imaged 128, 130 then process 100 proceeds to step 132, and determines if the next image location uses the same superset of views identified at step 114. If so 132, 134, helical view weighting is applied at step 124 to the superset range of views or data so as to reconstruct an image for the next z-location. However, if the superset range of views previously identified at step 114 cannot or will not be used to generate images for the next z-location 132, 136 then process 100 returns to step 114 and a new superset range of views is queried and process 100 proceeds as to heretofore described until all z-locations have been properly imaged.

Application of the image location driven multiphase reconstruction described with respect to FIG. 5 affords significant savings in processing time. The amount of time savings will vary depending on the particular size of the cardiac study; however, the time savings may be upwards of 50%. This time savings is illustrated in the following example:

Example

Calibration processing and restoring the data from the disk can take 3 ms per view. A typical view range for a cardiac burst image at a phase location that needs to be calibration processed is 5000 views. So calibration processing time will be ~15 s. View weighting takes less than 0.5 sec per image. As a result, the first six images are imaged in 18 sec. Thereafter, for the next image location usually incremental acquisition data is needed in the order of 1000 views as the next set of z-locations will reuse some cardiac cycle from the previous set. So the time for next subsequent set of six images is around 6 sec. A typical study of 150 images will thus be done for a single phase in (18+6*144/6) sec ≈ 162 sec. Thus, for a multi phase study of 10 phases and 120 images using phase location driven reconstruction will take ≈ 1620 seconds the imaging steps must be repeated for each phase of the study.

In contrast, with the image location driven reconstruction, the time saving is significant. For making the first set of six z-location images at all the phase locations ~5500 views must be prepared. But with that data 60 images can now be made for the entire study. Time taken for this is: 16.5 s+0.5*60=46.5 s. For the incremental sets of next six locations at all phases the time needed is 3.3+0.5*60=33 sec. The overall time for 120 images at all phase locations will be 46.5+33*144/≈ 838 seconds. Compared to the phase location driven process illustrated above, this is a time savings of almost 50 percent.

Therefore, in one embodiment, the present invention includes a method of multi-phase cardiac images comprising the steps of acquiring views of image data for a number of prescribed phases for a number of imaging locations of a field-of-view (FOV) over a series of cardiac cycles of a subject and assessing operational parameters of an image reconstruction system. The method also includes the step of selecting, based on the operational parameters, one of a phase location driven reconstruction process that reconstructs images from views for all the number of imaging locations for one phase before reconstructing images for another phase and an image location driven reconstruction process that reconstructs images from views for all the prescribed phases for one imaging location before reconstructing images for another imaging location.

According to another embodiment, the present invention includes a CT cardiac imaging system comprises an EKG machine to obtain an EKG recording of a patient indicative of a cardiac cycle of the patient. The system further includes a CT imaging apparatus comprising a data acquisition module including a rotatable gantry having a bore therethrough designed to receive the patient being translated through the bore by a movable table, the rotatable gantry having an x-ray source and an x-ray detector disposed therein to emit a fan beam of x-rays toward the patient and receive x-rays attenuated by the patient, respectively. The CT imaging apparatus further includes a computer programmed to control the data acquisition module to acquire CT data of the patient as a function of the cardiac cycle of the patient and determine if the CT imaging apparatus supports an image driven location reconstruction process wherein images are generated for all phases of the cardiac cycle at a first location before generating images at a second location and, if not, initialize a default phase location driven reconstruction process wherein images are generated at all locations for a first phase of the cardiac cycle before generating images for a second phase of the cardiac cycle.

In another embodiment, the invention includes a computer readable storage medium having a computer program to adaptively select between CT reconstruction techniques, the computer program representing a set of instructions that when executed by a computer causes the computer to execute one acquisition data restore from a disk and calibration processing for a set of views needed to reconstruct a series of images for a plurality of z-locations for all measured phases of a cardiac cycle. The set of instructions then causes the computer to determine at least a portion of the set of views that are needed for reconstructing images at a first z-location for all measured phases of the cardiac cycle and reconstruct an image at the first z-location for all measured phases of the cardiac cycle before reconstructing an image at a next z-location.

The present invention has been described in terms of the preferred embodiment, and it is recognized that equivalents, alternatives, and modifications, aside from those expressly stated, are possible and within the scope of the appending claims.

What is claimed is:

1. A method of multi-phase cardiac imaging comprising the steps of:
   acquiring views of image data for a number of prescribed phases for a number of imaging locations of a field-of-view (FOV) over a series of cardiac cycles of a subject;
   assessing operational parameters of an image reconstruction system; and
   selecting, based on the operational parameters, one of:
      a phase location driven reconstruction process that reconstructs images from views for all the number of imaging locations for one phase before reconstructing images for another phase; and
      an image location driven reconstruction process that reconstructs images from views for all the prescribed phases for one imaging location before reconstructing images for another imaging location.

2. The method of claim 1 wherein the operational parameters include hardware specifications of the reconstruction system.

3. The method of claim 2 wherein the step of assessing further includes the step of determining if the reconstruction system includes sufficient buffer space to support the image location driven reconstruction process.

4. The method of claim 3 further comprising the step of implementing the image location driven process if the reconstruction process has a buffer sufficiently sized to store a calibrated superset of views, the superset including views for all the prescribed phases for all the imaging locations.

5. The method of claim 4 further comprising the step of applying a helical view-weighting algorithm to process only those views stored in the buffer needed to reconstruct an image at a particular phase and an imaging location.

6. The method of claim 1 further comprising the step of selecting further based on a user input on a GUI identifying at least one of an image location along a Z-direction in the FOV and a single phase of a cardiac cycle of the subject.

7. The method of claim 6 wherein the phase location driven reconstruction process comprises the steps of:
   (A) determining if the user-identified phase has correspondingly acquired views of image data;

(B) ascertaining range of views needed to generate an image at the user-identified phase;
(C) applying weighting factors to acquired views for the user-identified phase;
(D) reconstructing an image for all locations in the FOV for the user-identified phase; and
(E) repeating steps (A)-(D) for a next user-identified phase of the cardiac cycle of the subject.

8. The method of claim 6 wherein the image location driven reconstruction process comprises the steps of:
(A) determining if the user-identified image location has correspondingly acquired views of image data;
(B) determining range of views needed to generate an image at the user-identified location for all the prescribed phases;
(C) applying weighting factors to range of views;
(D) reconstructing an image at the user-defined location for all the prescribed phases; and
(E) repeating steps (A)-(D) for a next user-identified image location in the z-direction.

9. A CT cardiac imaging system comprising:
an EKG machine to obtain an EKG recording of a patient indicative of a cardiac cycle of the patient;
a CT imaging apparatus comprising a data acquisition module including a rotatable gantry having a bore therethrough designed to receive the patient being translated through the bore by a movable table, the rotatable gantry having an x-ray source and an x-ray detector disposed therein to emit a fan beam of x-rays toward the patient and receive x-rays attenuated by the patient, respectively, and the CT imaging apparatus further comprising a computer programmed to:
control the data acquisition module to acquire CT data of the patient as a function of the cardiac cycle of the patient;
determine if the CT imaging apparatus supports an image driven location reconstruction process wherein images are generated for all phases of the cardiac cycle at a first location before generating images at a second location; and if not
initialize a default phase location driven reconstruction process wherein images are generated at all locations for a first phase of the cardiac cycle before generating images for a second phase of the cardiac cycle.

10. The CT cardiac imaging system of claim 9 wherein the computer is further programmed to apply the image location driven reconstruction process if the CT imaging apparatus has sufficient memory to store calibrated CT data for all phases of the cardiac cycle at all locations.

11. The CT cardiac imaging system of claim 10 wherein the computer is further programmed to identify the first location based on a user input to a GUI displayed on a monitor of the CT imaging apparatus.

12. The CT cardiac imaging system of claim 11 wherein the computer is further programmed to query and find a range of views needed to generate images for all phases of the cardiac cycle at the user-identified first location.

13. The CT cardiac imaging system of claim 12 wherein the computer is further programmed to scan data from memory for the range of views, calibrate scanned data, store calibrated scanned data in a projection buffer, and apply helical weighting to the calibrated scanned data.

14. The CT cardiac imaging system of claim 13 wherein the computer is further programmed to determine if a next user-identified location uses same range of views used for the first location and, if so, generate an image for all phases at the next user-identified location from the same range of views and, if not, query and find range of views needed to generate image at the next user-identified location.

15. A non-transitory computer readable storage medium having a computer program to adaptively select between CT reconstruction techniques, the computer program representing a set of instructions that when executed by a computer causes the computer to:
execute one acquisition data restore from a disk and calibration processing for a set of views needed to reconstruct a series of images for a plurality of z-locations for all measured phases of a cardiac cycle;
determine at least a portion of the set of views that are needed for reconstructing images at a first z-location for all measured phases of the cardiac cycle; and
reconstruct an image at the first z-location for all measured phases of the cardiac cycle.

16. The computer readable storage medium of claim 15 wherein the set of instructions further causes the computer to:
assess operational parameters of a CT system;
determining from the operational parameters if the CT system supports execution of an image location driven multi-phase cardiac reconstruction wherein images at the first z-location are reconstructed for all the measured phases before reconstructing images at a second z-location; and if the CT system does not support the image location driven multi-phase cardiac reconstruction
execute a phase location driven multi-phase cardiac reconstruction wherein images are reconstructed for all measured z-locations at a first phase before reconstructing images for a second phase.

17. The computer readable storage medium of claim 16 wherein the set of instructions further causes the computer to determine which reconstruction the CT system supports by determining if the CT system has sufficient temporary memory to hold calibrated CT scan data corresponding to all the measured phases of a cardiac cycle at all z-locations.

18. The computer readable storage medium of claim 17 wherein the set of instructions further causes the computer to generate an image for all phases at the first z-location by applying helical view weighting to only those views stored in the temporary memory that correspond to all the measured phases at the first z-location.

19. The computer readable storage medium of claim 17 wherein sufficient temporary memory is a function of the plurality of z-locations and the number of measured phases.

20. The computer readable storage medium of claim 17 wherein the set of instructions further causes the computer to independently select those views stored in the temporary memory that correspond to all the measured phases at the first z-location to generate an image for all phases at the first z-location.

21. The computer readable storage medium of claim 16 wherein the set of instructions further causes the computer to execute the image location driven multi-phase cardiac reconstruction independent of cardiac image type.

* * * * *